(12) United States Patent
Krumbein et al.

(10) Patent No.: US 10,791,589 B2
(45) Date of Patent: Sep. 29, 2020

(54) SENSOR CIRCUIT AND METHOD FOR COMPENSATING FOR TEMPERATURE CHANGES

(71) Applicant: Infineon Technologies AG, Neubiberg (DE)

(72) Inventors: Ulrich Krumbein, Rosenheim (DE); Werner Simbuerger, Haar (DE); Dietmar Straeussnigg, Villach (AT); Andreas Wiesbauer, Poertschach (AT)

(73) Assignee: INFINEON TECHNOLOGIES AG, Neubiberg (DE)

( * ) Notice: Subject to any disclaimer, the term of this patent is extended or adjusted under 35 U.S.C. 154(b) by 376 days.

(21) Appl. No.: 15/879,110

(22) Filed: Jan. 24, 2018

(65) Prior Publication Data
US 2018/0213602 A1 Jul. 26, 2018

(30) Foreign Application Priority Data
Jan. 26, 2017 (DE) .......................... 10 2017 101 498

(51) Int. Cl.
*H05B 3/02* (2006.01)
*G01L 9/12* (2006.01)
*G01L 19/00* (2006.01)
*H05B 1/02* (2006.01)
*G01K 1/20* (2006.01)
(Continued)

(52) U.S. Cl.
CPC ................ *H05B 3/02* (2013.01); *G01K 1/20* (2013.01); *G01L 9/125* (2013.01); *G01L 19/0092* (2013.01); *G01L 19/04* (2013.01); *G01N 33/0073* (2013.01); *H04R 1/08* (2013.01); *H05B 1/0227* (2013.01); *H04R 9/022* (2013.01); *H04R 2201/003* (2013.01)

(58) Field of Classification Search
CPC ..... G01L 9/125; G01L 19/0092; G01L 19/04; H05B 3/02; H05B 1/0227; G01K 1/20; G01N 33/0073; H04R 1/08; H04R 2201/003; H04R 9/022
See application file for complete search history.

(56) References Cited

U.S. PATENT DOCUMENTS

2003/0174005 A1* 9/2003 Latham, II ............ H02M 3/157
                                                              327/172
2007/0229176 A1* 10/2007 Fukuda .................... H03B 5/04
                                                              331/158
(Continued)

FOREIGN PATENT DOCUMENTS

DE         10025440 A1   12/2001
DE         69926610 T2    6/2006
(Continued)

*Primary Examiner* — David P Angwin
*Assistant Examiner* — Bob Zadeh
(74) *Attorney, Agent, or Firm* — Slater Matsil, LLP

(57) ABSTRACT

A sensor circuit and a method for compensating for temperature changes are provided. In accordance with an embodiment, sensor circuit includes at least one sensor for determining a measurement variable; a heating structure; and at least one compensation circuit. The compensation circuit is configured to acquire information about a temperature change in an environment of the sensor, and to counteract a temperature change in the sensor on the basis of the information by driving the heating structure.

19 Claims, 5 Drawing Sheets

(51) Int. Cl.
*G01L 19/04* (2006.01)
*G01N 33/00* (2006.01)
*H04R 1/08* (2006.01)
*H04R 9/02* (2006.01)

(56) References Cited

U.S. PATENT DOCUMENTS

| | | | |
|---|---|---|---|
| 2010/0015933 A1* | 1/2010 | Kerselaers | H03G 3/3042 |
| | | | 455/127.2 |
| 2015/0156054 A1* | 6/2015 | Hirano | H04L 27/364 |
| | | | 455/102 |
| 2015/0180410 A1* | 6/2015 | Yamamoto | H03B 5/04 |
| | | | 331/70 |
| 2016/0241190 A1* | 8/2016 | Itasaka | H03B 5/364 |
| 2018/0213602 A1* | 7/2018 | Krumbein | G01K 1/20 |

FOREIGN PATENT DOCUMENTS

| | | |
|---|---|---|
| DE | 102010005671 B3 | 6/2011 |
| DE | 102014214432 A1 | 1/2016 |
| DE | 102016203228 A1 | 9/2016 |
| EP | 1157868 A2 | 11/2011 |

\* cited by examiner

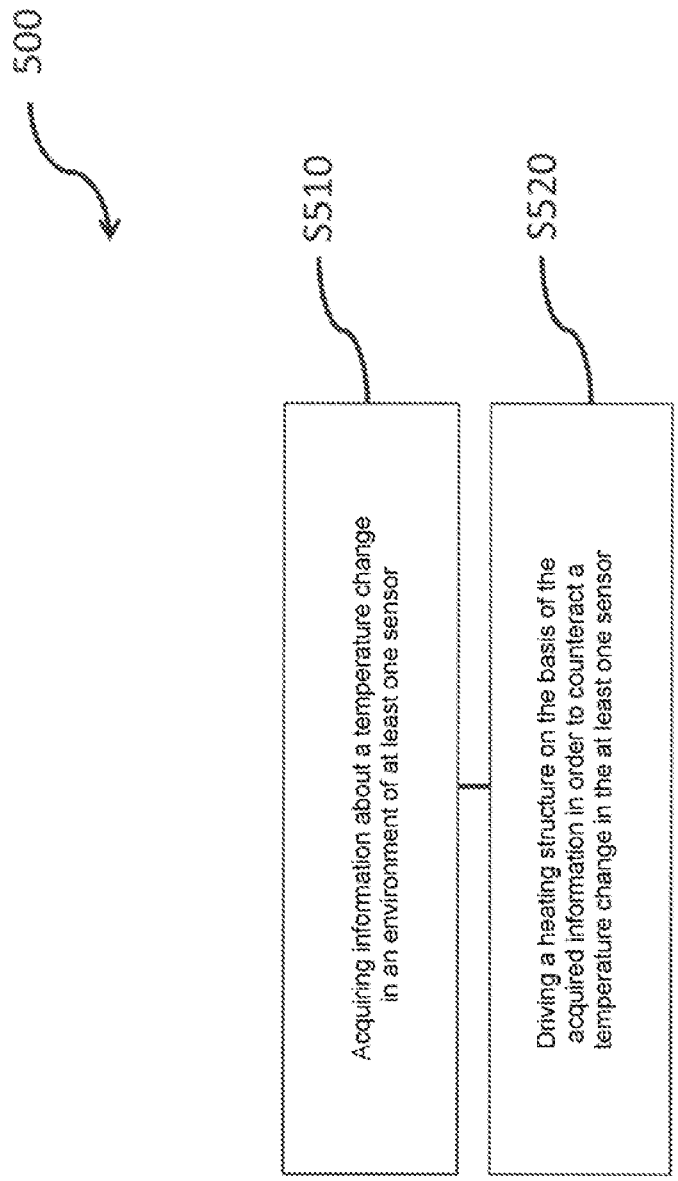

SENSOR CIRCUIT AND METHOD FOR COMPENSATING FOR TEMPERATURE CHANGES

CROSS-REFERENCE TO RELATED APPLICATIONS

This application claims the benefit of German Application No. 102017101498.5, filed on Jan. 26, 2017, which application is hereby incorporated herein by reference in its entirety.

TECHNICAL FIELD

Exemplary embodiments relate to a sensor circuit and to a method for compensating for temperature changes.

BACKGROUND

A sensor in a sensor circuit, for example in a Micro-Electro-Mechanical System (MEMS) or in an application-specific integrated circuit (ASIC), can be influenced by external influences, for example by an influencing of the sensor by one electronic device or by a plurality of electronic devices in the environment of the sensor.

If the sensor is situated in the vicinity of one electronic device or a plurality of electronic devices, for example of a power amplifier or of an antenna of a mobile telephone or of a further sensor, the sensor can be adversely influenced by the power amplifier or the antenna in such a way that the sensor undesirably reflects an activity of the further device or of the further devices in its environment.

Heating of an environment of the sensor or heating of the sensor, i.e. a temperature increase in the sensor, can be established on account of the external influencing of the sensor as a result of an activity or operation of an external electronic device. Cooling of an environment of the sensor or of the sensor, i.e. a temperature decrease in the sensor, can be established on account of the external influencing of the sensor on account of an inactivity or stopping of operation of an external device.

The temperature change causes interference signals superimposed on the measurement signals and leads to an undesired corruption of the sensor measurement signals.

In this context, this is also referred to as "XT", "X-talk" or "cross-talk". This is a term that generally denotes the undesired influencing of signals which per se are independent of one another.

By way of example, in the case of a microphone whose temperature is influenced by a heating power of a further device, a heating power of less than approximately 100 μW can suffice to cause audible X-talk in the microphone (this may also be referred to as a thermoacoustic effect). The temperature change here is less than approximately 1 mK and cannot usually be measured and used as an input signal for compensating for a temperature change. A signal purged of a thermal interference variable may be designated in the present case as a thermal-X-talk-compensated signal.

There is thus a need for a sensor circuit and a method for compensating for temperature changes in an environment of a sensor by means of which such a temperature influencing or X-talk can be kept in a predefined tolerance range or can be reduced or possibly even minimized.

SUMMARY

In accordance with an embodiment, a sensor circuit includes at least one sensor for determining a measurement variable; a heating structure; and at least one compensation circuit. The compensation circuit is configured to acquire information about a temperature change in an environment of the sensor, and to counteract a temperature change in the sensor on the basis of the information by driving the heating structure.

In a further embodiment, a method for compensating for temperature changes includes acquiring information about a temperature change in an environment of at least one sensor; and driving a heating structure on the basis of the acquired information in order to counteract a temperature change in the at least one sensor.

BRIEF DESCRIPTION OF THE DRAWINGS

Some embodiments of devices and/or methods that serve as an example are explained in greater detail below merely as an example and with reference to the appended figures, in which:

FIG. 5 shows a flow diagram of a method for compensating for a temperature change in accordance with various exemplary embodiments.

DETAILED DESCRIPTION OF ILLUSTRATIVE EMBODIMENTS

In the following detailed description, reference is made to the accompanying drawings, which form part thereof and which show for illustration purposes specific embodiments in which the invention can be implemented. In this regard, direction terminology such as, for instance, "at the top", "at the bottom", "at the front", "at the back", "front", "rear", etc., is used with regard to the orientation of the figure(s) described. Since components of embodiments can be arranged in a number of different orientations, the direction terminology serves for illustration and is not restrictive in any way whatsoever.

It goes without saying that other embodiments can be used and structural or logical changes can be made, without departing from the scope of protection of the various exemplary embodiments. It goes without saying that the features of the various exemplary embodiments described herein can be combined with one another, unless specifically indicated otherwise.

The following detailed description should therefore not be interpreted in a restrictive sense, and the scope of protection of the present invention is defined by the appended claims. In the figures, the thicknesses of lines, layers and/or regions may be exaggerated for reasons of clarity.

Even though further exemplary embodiments may accordingly have various modifications and alternative forms, some embodiments thereof serving as an example are illustrated by way of example in the figures and are described in detail here. It goes without saying, however, that the intention is not to limit embodiments serving as an example to the specific forms disclosed, rather on the contrary exemplary embodiments serving as an example are intended to cover all modifications, equivalent configurations and alternatives that fall within the scope of protection of the invention. In the description of the figures, identical numerals refer to identical or similar elements.

In the context of this description, the terms "connected" and "coupled" are used to describe both a direct and an indirect connection, and a direct or indirect coupling. In the figures, identical or similar elements are provided with identical reference signs, insofar as this is expedient.

The terminology used here serves only to describe specific embodiments serving as an example and is not intended to have a limiting effect for further embodiments serving as an example. Here the singular forms "a", "an" and "the" are also intended to include the plural forms, unless clearly indicated otherwise in the context. It should furthermore be noted that the terms "comprises", "comprising", "has" and/or "having", if used here, specify the presence of mentioned features, integers, steps, operations, elements and/or components, but do not exclude the presence or addition of one or more other features, integers, steps, operations, elements, components and/or groups thereof.

Figure 1:
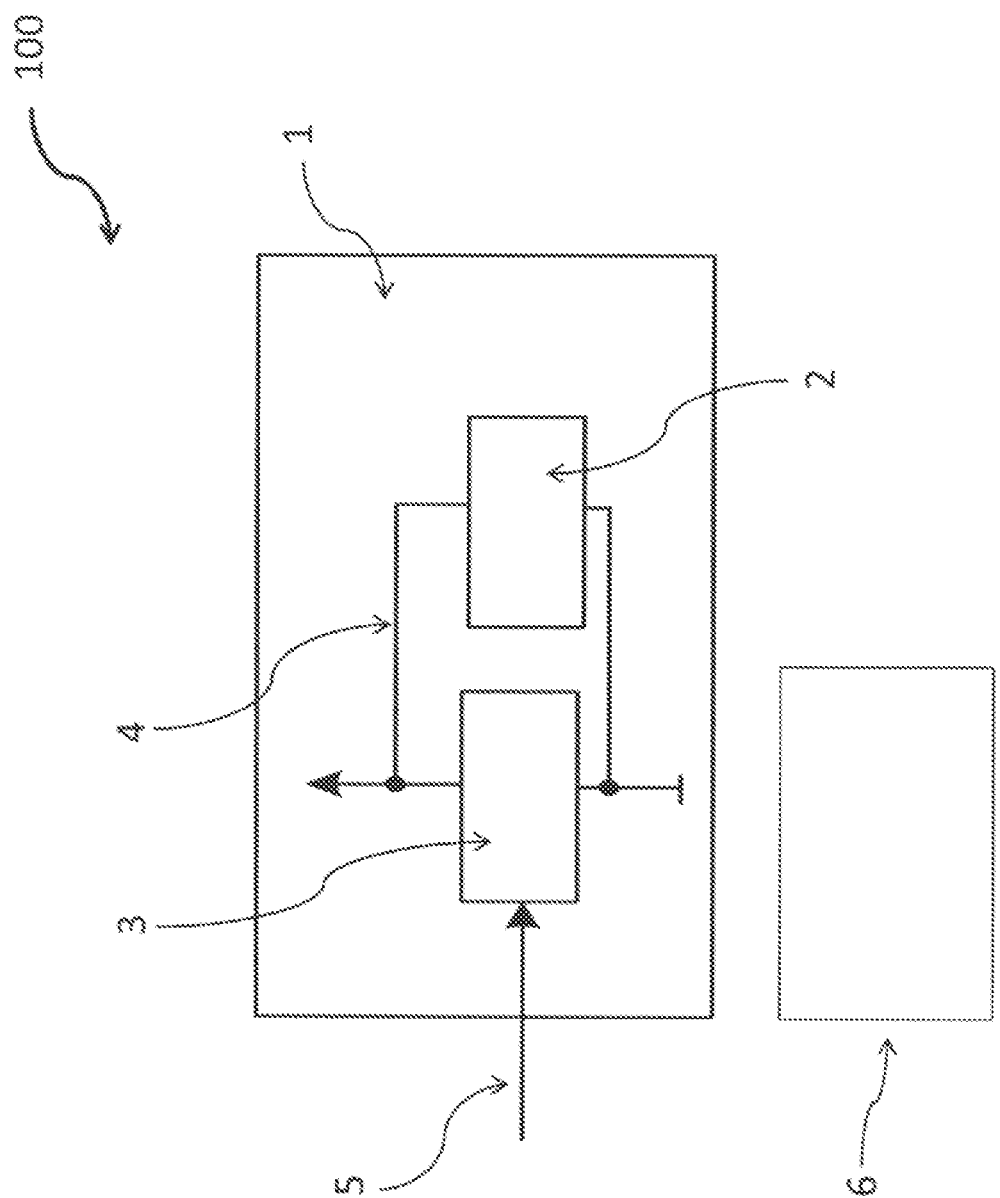
FIG. 1 shows a block diagram of a sensor circuit in accordance with various exemplary embodiments.

FIG. 1 shows a block diagram 100 of a sensor circuit 1 in accordance with various exemplary embodiments. The sensor circuit 1 can comprise a sensor 2 and a compensation circuit 3. As illustrated in FIG. 1, the sensor 2 can be coupled by means of lines 4 between a supply voltage or voltage source. The compensation circuit 3 can be coupled by means of lines 4 between a supply voltage. The sensor circuit 1 can be a MEMS or an ASIC or a MEMS with an ASIC coupled thereto. The sensor circuit 1 can be provided for example in a smartphone or tablet.

The compensation circuit 3 can be permanently supplied with a voltage by means of the supply voltage in such a way that, during operation of the sensor circuit 1, a current can flow through a heating structure provided in the compensation circuit 3 and a power loss in the form of heat can be generated by means of the heating structure.

By way of example, the sensor 2 and the compensation circuit 3 can be connected in parallel, as is illustrated by way of example in FIG. 1.

By means of information 5 about a temperature change or about an activity or operation of an external device 6, the compensation circuit 3 can variably set or adapt the heating structure, such that, by means of the heating structure, by way of example, a decrease in the power loss of the device 6 can be counteracted by means of an increase in the power loss of the heating structure, and vice versa.

The information 5 can comprise for example information regarding operation of a power amplifier and/or of an antenna in a smartphone or a tablet. Furthermore, a radio-frequency power amplifier envelope signal or a time division multiple access (TDMA) signal can also be received as information 5. The information 5 can be provided in an environment of the sensor circuit 1 (to put it another way sensor-circuit-externally, for example sensor-externally).

By means of the received information 5 it is possible to ascertain when one device 6 or a plurality of devices 6 is/are active or in operation. Furthermore, the information 5 can be a signal of a temperature sensor which is provided in an environment of the sensor and detects an ambient temperature or an ambient temperature change as a result of a device 6.

The sensor 2 can be or comprise at least one of a microphone, a temperature sensor, a pressure sensor or a gas sensor. The at least one sensor 2 can be accommodated together with the heating structure in a package or housing. The compensation circuit 3 can be configured to counteract a temperature change in an environment of the sensor 2 or in the sensor 2 by means of a change in a power loss of the heating structure.

Figure 2:
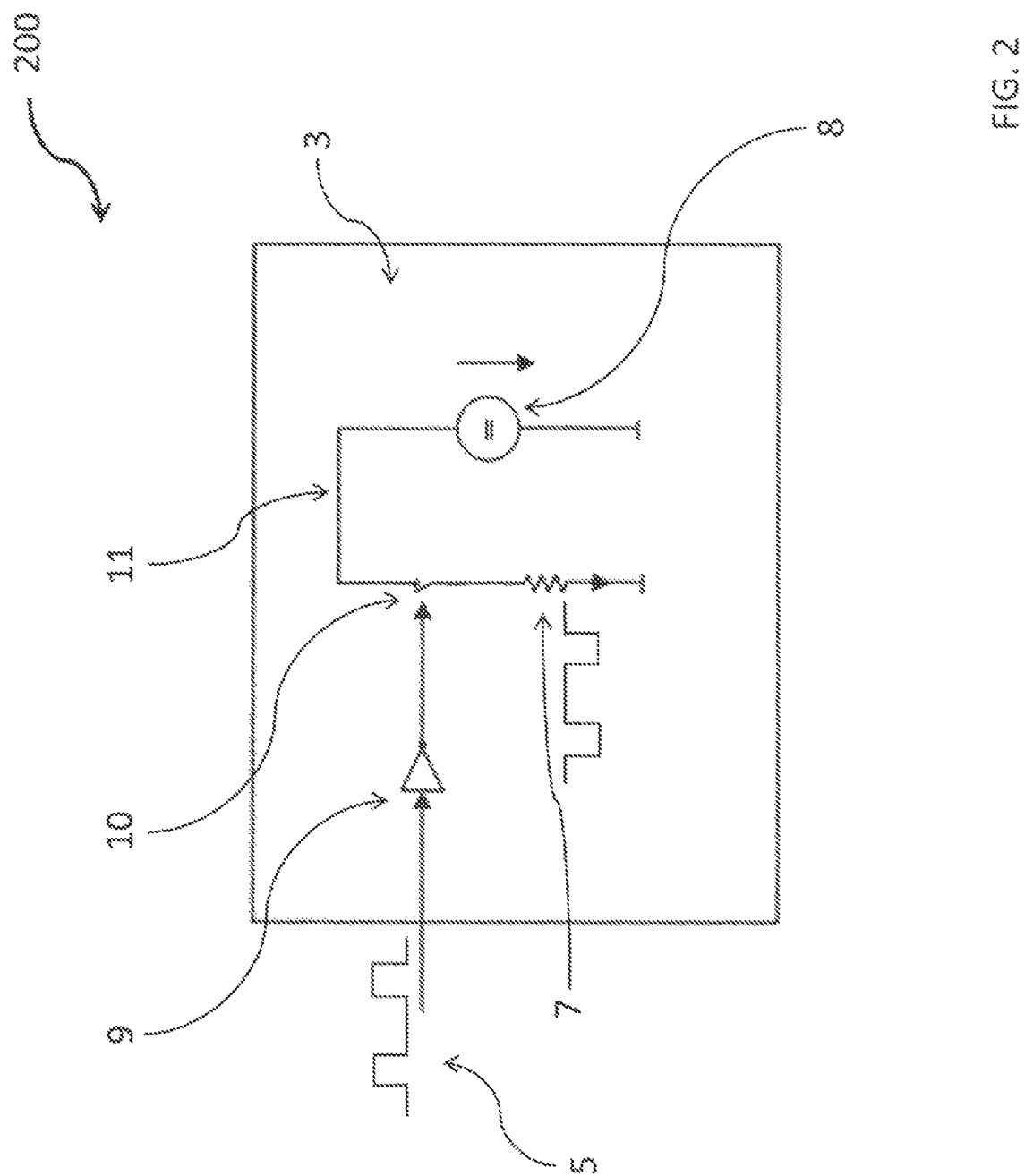
FIG. 2 shows a block diagram of a compensation circuit in accordance with various exemplary embodiments.

FIG. 2 shows a block diagram 200 of a compensation circuit 3 in accordance with various exemplary embodiments.

A switch-on/switch-off sequence can be provided to the compensation circuit 3 as external information 5 about an activity or operation of at least one device 6. The information 5 can be used to ascertain whether the at least one device 6 is switched on or whether the at least one device 6 is switched off. If the external information 5 is a switch-on/switch-off sequence, the switch-on/switch-off sequence can be compensated for by an opposite switch-on/switch-off sequence of the at least one heating structure 7. The power loss of a heating structure 7, for example a resistor, can be described in accordance with the equation:

$$P_{loss} = \frac{V_{reference}^2}{R_{heating}}$$

$P_{loss}$ can be a power loss and have the unit of measurement of watts (W). $V_{reference}$ can be a reference voltage and have the unit of measurement of volts (V). $R_{heating}$ can be a resistance value of the heating structure 7 and have the unit of measurement of ohms (a).

However, the heating structure 7 can also be realized as a variable resistor or as a field effect transistor, for example a metal oxide semiconductor field effect transistor, or as a field effect transistor array.

If a current flows through the heating structure 7, then a power loss in the form of heat is generated. The heat can then be used to heat one sensor 2 or a plurality of sensors. If no current flows through the heating structure 7 and thus no power loss in the form of heat can be generated, a temperature of the sensor 2 or of the sensors can be reduced.

In detail, the compensation circuit 3 receives a switch-on/switch-off sequence as information 5, which is fed to an inverter 9 as input signal. The inverter 9 inverts or negates the received input signals as information 5 and forwards the inverted switch-on/switch-off sequence of the signals to a switching device 10, for example. The switching device 10 is realized as an actuator which can open or close a circuit 11, for example. The switching device 10 can be an electromechanically actuatable switch.

The circuit 11 can comprise the heating structure 7, the supply voltage 8 and the switching device 10. The heating structure 7, the supply voltage 8 and the switching device 10 can be provided for example in a series connection, as is illustrated by way of example in FIG. 2.

If a switch-off signal or a switch-off level or no signal or a state "0" is present as information 5, the signal is inverted by means of the inverter 9. In that case a "1" is present at the output of the inverter 9 and the switching device 10 is activated. The circuit 11 is closed by means of the switching device 10 and a current $$I = \frac{V_{reference}}{R_{heating}}$$

flows. By means of the current and the resistance of the heating structure 7, a power loss of $$P_{loss} = \frac{V_{reference}^2}{R_{heating}}$$

is generated. If the heating structure 7 was switched off, for example, then a temperature of the heating structure 7 can be increased upon operation of the heating structure 7. The heating structure 7 can generate a defined power loss during operation, such that the sensor 2 is kept constantly at a predefined temperature depending on a predefined power loss of the heating structure 7.

Given the presence of a switch-on signal or switch-on level or given a state "1", the switching device 10 is deactivated by means of the signal "0" present at the output of the inverter 9, such that the circuit 11 is opened (see FIG. 2). On account of the circuit 11 having been opened, a current cannot flow through the heating structure 7 and no power loss $P_{loss}$ can be generated by the heating structure 7. The temperature of the heating structure 7 can consequently decrease, and thus so can the temperature of the sensor 2. The switching device 10 can be realized for example as an electromechanically actuatable switch, as a relay, as a break contact, as a make contact, as a field effect transistor (FET) or as a bipolar transistor.

Figure 3:
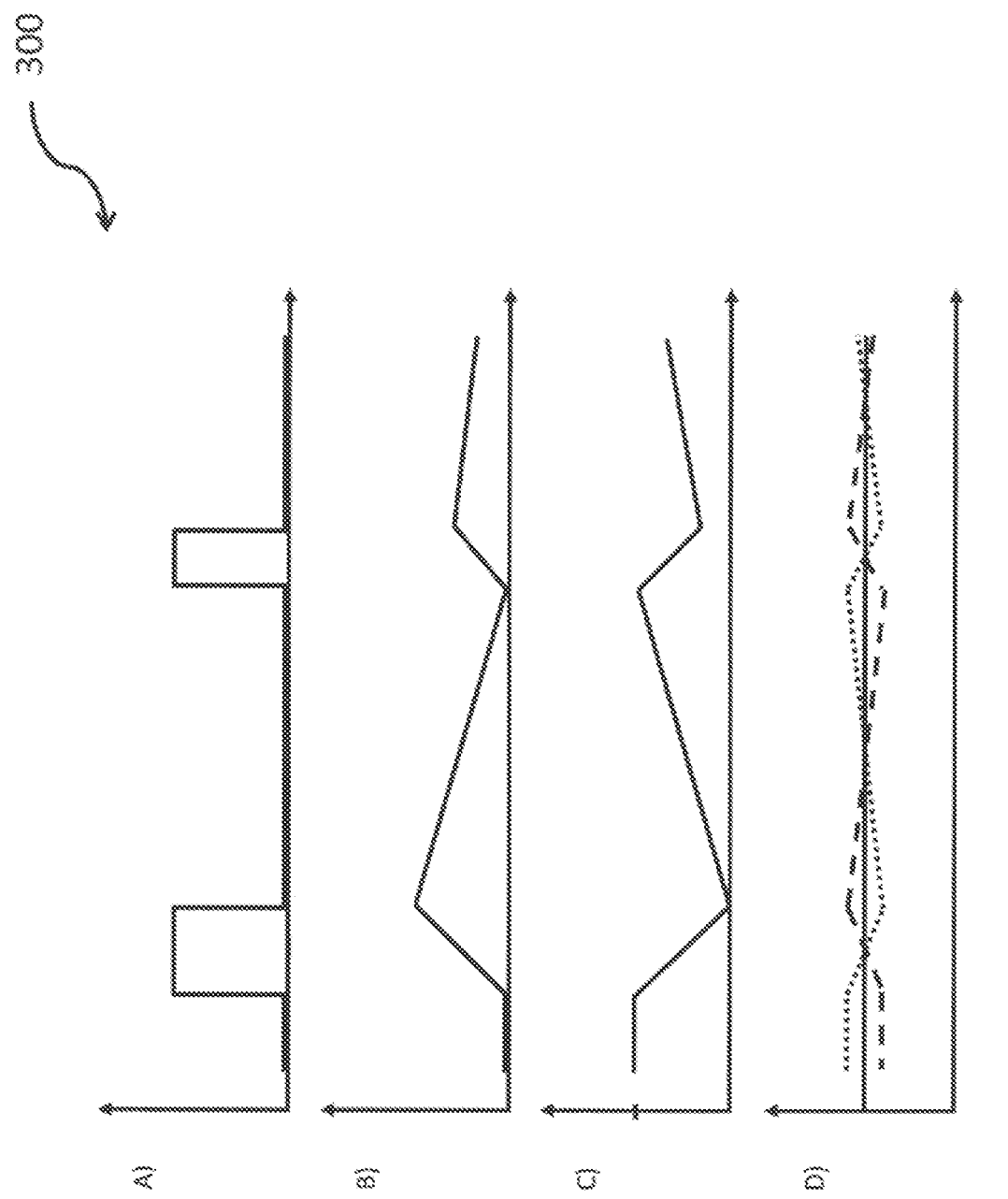
FIG. 3 shows a plurality of exemplary diagrams of a method for compensating for a temperature change in accordance with various exemplary embodiments.

FIG. 3 shows exemplary diagrams of a method for compensating for a temperature change in accordance with various exemplary embodiments.

In detail, a diagram A) illustrates a profile of a signal as information about an activity or operation of an external device 6 against time. The signal can be for example a switch-on and switch-off sequence of a device or can represent an external activity, there being no signal if no external activity of a device is present. A constant signal is present if an activity of an external device 6 is present.

At the beginning, no activity of an external device 6, for example no operation of a device 6, may be present, as is illustrated by way of example in diagram A) in FIG. 3. As a result of activation or operation of the at least one external device 6, an activity of the external device 6 may be present as information for an arbitrary time.

A further exemplary diagram B) illustrates a profile of a temperature of a sensor 2 or a result of heating of a sensor 2 on account of an activity of an external device 6 against time. If no external activity of a device 6 is present, then no power loss in the form of heat is generated either. It is evident that the sensor 2 heats up after activation of an external device 6 until the point in time at which the external device 6 is deactivated. The sensor 2 heats up all the more, the longer an activity of an external device 6 is present. If the external device 6 is deactivated, then a temperature of the sensor 2 decreases again. If further activity of an external device 6 no longer occurs, then the temperature of the sensor 2 decreases down to the initial temperature of the sensor 2.

A further exemplary diagram C) illustrates a profile of a temperature of a variable heating structure 7 against time. A behavior of the heating structure 7 in response to the temperature change in the sensor 2 is evident. The variable heating structure 7 generates a predefined power loss during operation in which no activity of an external device can be detected. The sensor 2 has a defined initial temperature for example as a result of the predefined power loss of the heating structure 7 in the form of heat.

If an activation of an external device 6 occurs and a temperature change, for example a temperature increase, in the sensor 2 thereupon occurs, than the power loss of the heating structure 7 is reduced in order to compensate for the temperature change or the temperature increase at the sensor 2. If an activity of an external device 6 is no longer present, then the power loss of the heating structure 7 can increase again, for example up to the initial temperature of the sensor 2. The temperature change in the heating structure 7 changes in the opposite direction to the temperature change in the sensor 2, in order to achieve a temperature compensation.

A further diagram D) illustrates overall temperature profiles at a sensor 2 in the case of an ideal state, in the case of overcompensation and in the case of under compensation by means of the heating structure 7 against time. In this case, the solid line represents an ideal state. The dotted line represents overcompensation and the dashed line represents under compensation.

Figure 4:
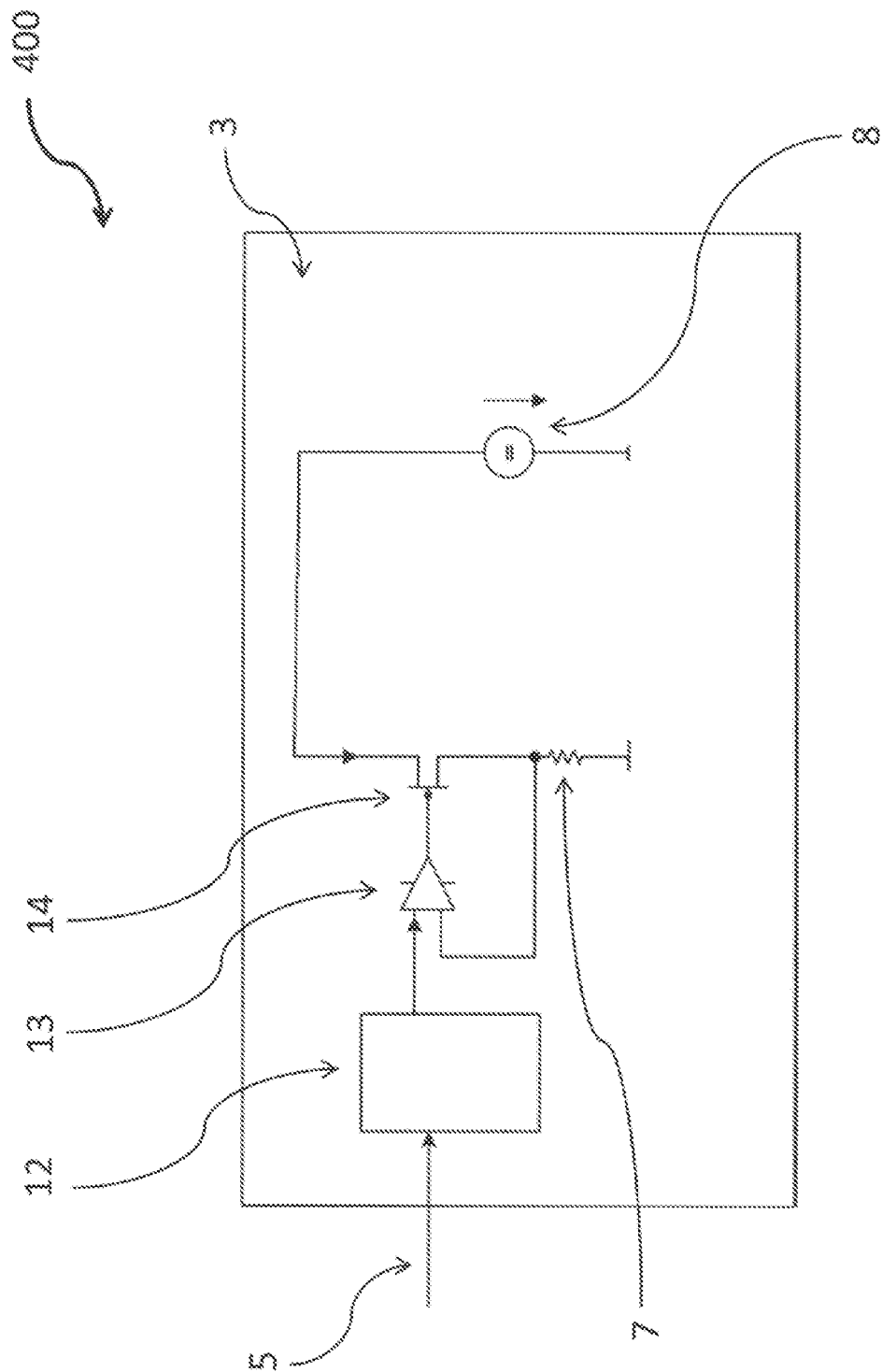
FIG. 4 shows a block diagram of a compensation circuit in accordance with various exemplary embodiments.

FIG. 4 shows a block diagram 400 of a compensation circuit 3 in accordance with various exemplary embodiments. The compensation circuit 3 comprises a digital-to-analog converter 12, an amplifier 13, a transistor as a switching device 14, a resistor as a heating structure 7, and a supply voltage 8. The digital-to-analog converter 12 receives information 5 as digital signals. The digital signals are or comprise information regarding an activity or operation of an external device 6 or a power loss of an external device 6. The digital-to-analog converter 12 converts the information 5 into analog signals. The analog signals are fed as input signals to the amplifier 13, for example a differential amplifier. A transistor 14 is driven by means of an output signal of the amplifier 13. The transistor 14 can be for example a p-channel junction field effect transistor. However, the present exemplary embodiment is not restricted thereto and other transistor embodiments or electromechanical switching systems are also able to be realized.

The transistor 14 can be coupled to the heating structure 7 and the supply voltage 8 in a series connection. The further input of the amplifier 13 taps off a voltage above the heating structure 7, for example between the source terminal of the transistor 14 and the heating structure 7, as is illustrated by way of example in FIG. 4.

The transistor 14 can comprise for example a drain terminal, a gate terminal and a source terminal. The transistor 14 can be connected in series with the heating structure 7 and the supply voltage 8 at the drain terminal and at the source terminal. The gate terminal of the transistor 14 can be coupled to the output of the amplifier 13. If a voltage is present at the output of the amplifier 13, then the transistor 14 is turned on and an electric circuit comprising the heating structure 7 and the supply voltage 8 and the transistor 14 is closed. The supply voltage 8 is provided such that a current can flow through the heating structure 7 when the transistor 14 is turned on, in order to generate a power loss in the form of heat by means of the heating structure 7.

In the exemplary embodiment illustrated with reference to FIG. 4, in the case of a gate-source voltage of 0V, no power loss can be generated by means of the heating structure 7. If the amplifier 13, which can be a differential amplifier, for example, outputs a voltage at its output, then a gate-source voltage of greater than 0V is established at the transistor 14. The transistor 14 is turned on. The gate-source voltage at the transistor 14, also referred to as control voltage, brings about a formation of a current between the drain and source terminals of the transistor 14. The current flows through the heating structure 7 and a power loss in the form of heat can be generated by means of the heating structure 7. If no voltage (0V) is present at the output of the amplifier 13, then the transistor 14 is turned off, for which reason no current can flow in the circuit and the heating structure 7 cannot generate power loss in the form of heat.

In various exemplary embodiments, a power loss can be described in accordance with the equation $$P_{loss} = I_{loss} * V_{reference} \sim \text{ext.activity} * K * V_{reference}$$

$P_{loss}$ can be a power loss. $I_{loss}$ can be a current loss which can lead to the power loss $P_{loss}$. $V_{reference}$ can be a reference voltage. $P_{loss}$ is equal to a product of the current loss $I_{loss}$ and the reference voltage $V_{reference}$. $P_{loss}$ can be proportional to a product of an external activity ext.activity, a gain factor K of an amplifier 13 and a supply voltage or reference voltage $V_{reference}$ 8 (see FIG. 4).

In the exemplary embodiment described with reference to FIG. 4, a complicated heating profile of an external device 6 can be compensated for since the information 5 about an external activity of a device 6 is made available to the compensation circuit 3 digitally.

FIG. 5 shows a flow diagram of a method for compensating for a temperature change in accordance with various exemplary embodiments. The method can comprise: acquiring information about a temperature change in an environment of at least one sensor (S510) and driving a heating structure on the basis of the acquired information in order to counteract a temperature change in the at least one sensor (S520).

In various exemplary embodiments, acquiring information can comprise receiving information regarding an activity or operation of a power amplifier and/or regarding an activity or operation of an antenna in a smartphone or in a tablet. Furthermore, the information can be provided and processed as a radio-frequency power amplifier envelope signal or a time division multiple access (TDMA) signal of a power amplifier.

Information about a temperature change in an environment of at least one sensor, for example around the sensor or around a package in which the at least one sensor is accommodated, can be acquired by means of the method.

By means of the method, a temperature change of a sensor temperature can be counteracted in the opposite direction by means of a heating structure using power loss, such that a sensor temperature can be kept in a predefined temperature range. What can thus be achieved is that a thermoacoustic effect can be reduced, possibly minimized. Furthermore, what can be achieved is that a measurement signal corruption of a sensor by thermal influences can be kept small.

Example 1 is a sensor circuit. The sensor circuit can comprise at least one sensor for determining a measurement variable, a heating structure, at least one compensation circuit, wherein the compensation circuit is configured to acquire information about a temperature change in an environment of the sensor, and to counteract a temperature change in the sensor on the basis of the information by means of driving the heating structure.

In the case of example 2, the subject matter of example 1 can optionally comprise a package, wherein the at least one sensor, the heating structure and the compensation circuit are accommodated in the package.

In the case of example 3, the subject matter of example 2 can optionally comprise the fact that the sensor circuit comprises a plurality of sensors in the package.

In the case of example 4, the subject matter of any of examples 1 to 3 can optionally comprise the fact that the sensor is at least one of a microphone, a temperature sensor, a pressure sensor or a gas sensor.

In the case of example 5, the subject matter of any of examples 1 to 4 can optionally comprise the fact that the compensation circuit is configured to counteract the temperature change by means of a change in a power loss of the heating structure.

In the case of example 6, the subject matter of any of examples 1 to 5 can optionally comprise the fact that the compensation circuit is provided alongside the at least one sensor in the sensor circuit.

In the case of example 7, the subject matter of any of examples 1 to 6 can optionally comprise the fact that the compensation circuit is configured to acquire the information about the temperature change in the environment of the sensor in the form of a periodic and/or a discrete switch-on and switch-off sequence, and wherein the compensation circuit is furthermore configured to activate or to deactivate the heating structure oppositely to the switch-on and switch-off sequence.

In the case of example 8, the subject matter of any of examples 5 to 7 can optionally comprise the fact that the compensation circuit is provided to compensate for a temperature increase in the environment of the sensor by means of reducing the power loss of the heating structure, and to compensate for a temperature reduction in the environment of the sensor by means of increasing the power loss of the heating structure.

In the case of example 9, the subject matter of any of examples 5 to 8 can optionally comprise the fact that the heating structure comprises at least one variable resistor, wherein the at least one variable resistor generates the power loss, or that the heating structure comprises at least one field effect transistor, optionally a metal oxide semiconductor field effect transistor, wherein the at least one field effect transistor is configured to generate the power loss.

In the case of example 10, the subject matter of any of examples 1 to 9 can optionally comprise the fact that the heating structure comprises at least one distributed digital field effect transistor array, optionally a metal oxide semiconductor field effect transistor array, having a nonuniform distribution of a compensating heating power in the array, wherein the at least one distributed digital field effect transistor array is configured to generate the power loss.

In the case of example 11, the subject matter of any of examples 1 to 10 can optionally comprise the fact that the compensation circuit comprises a switching device, a voltage supply and the heating structure in a series connection.

In the case of example 12, the subject matter of example 11 can optionally comprise the fact that the compensation circuit furthermore comprises an inverter, wherein the inverter is connected upstream of the switching device, and the switching device is an electromechanically actuatable switch.

In the case of example 13, the subject matter of example 11 can optionally comprise the fact that the compensation circuit furthermore comprises a differential amplifier and a digital-to-analog converter, wherein the differential amplifier is connected upstream of the switching device and an input of the differential amplifier is coupled to an output of the digital-to-analog converter, wherein the digital-to-analog converter is configured to acquire the information about the temperature change in the environment of the sensor circuit as a digital signal, wherein the differential amplifier is configured in such a way that an output signal of the differential amplifier activates or deactivates the switching device, and wherein the switching device is a transistor.

In the case of example 14, the subject matter of any of examples 1 to 13 can optionally comprise the fact that the sensor circuit is provided in a smartphone or in a tablet.

In the case of example 15, the subject matter of any of examples 1 to 14 can optionally comprise the fact that the sensor circuit is a Micro-Electro-Mechanical System (MEMS) or an application-specific integrated circuit (ASIC).

In the case of example 16, the subject matter of any of examples 1 to 15 can optionally comprise the fact that an envelope signal of a radio-frequency power amplifier is usable as the information or a time division multiple access (TDMA) signal of a power amplifier is usable as the information.

Example 17 is a method for compensating for temperature changes. The method can comprise acquiring information about a temperature change in an environment of at least one sensor, driving a heating structure on the basis of the acquired information in order to counteract a temperature change in the at least one sensor.

In the case of example 18, the subject matter of example 17 can optionally comprise the fact that acquiring the information comprises receiving information regarding operation of a power amplifier and/or regarding operation of an antenna in a smartphone or in a tablet.

In the case of example 19, the subject matter of example 17 can optionally comprise the fact that acquiring the information comprises receiving a radio-frequency power amplifier envelope signal or receiving a time division multiple access (TDMA) signal of a power amplifier.

In the case of example 20, the subject matter of any of examples 17 to 19 can optionally comprise the fact that driving the heating structure comprises counteracting a temperature increase in the environment of the at least one sensor by means of reducing the power loss of the heating structure, and wherein driving the heating structure comprises counteracting a temperature decrease in the environment of the at least one sensor by means of increasing the power loss of the heating structure.

In the case of example 21, the subject matter of example 20 can optionally comprise the fact that counteracting a temperature increase in the environment of the at least one sensor comprises deactivating the heating structure, and counteracting a temperature decrease in the environment of the at least one sensor comprises activating the heating structure.

In the case of example 22, the subject matter of any of examples 17 to 21 can optionally comprise the fact that acquiring the information and driving the heating structure are carried out dynamically.

In the case of example 23, the subject matter of any of examples 17 to 22 can optionally comprise the fact that the heating structure is driven in such a way that a temperature of at least one sensor is kept in a predefined temperature range, such that fluctuations of an output signal of the at least one sensor on account of the temperature change are kept in a predefined tolerance range.

In the case of example 24, the subject matter of any of examples 17 to 23 can optionally comprise the fact that a degree of compensation of temperature changes in a range of approximately 80% to approximately 90%, for example of approximately 85%, is achieved by means of the method.

In the case of example 25, the subject matter of any of examples 17 to 24 can optionally comprise the fact that a damping of an interference variable in a range of approximately 14 dB to approximately 20 dB, for example of approximately 17 dB, is achieved by means of the method.

In the case of example 26, the subject matter of any of examples 17 to 25 can optionally comprise the fact that, in the method, at least one variable resistor or at least one field effect transistor, optionally a metal oxide semiconductor field effect transistor, is used as the heating structure.

In the case of example 27, the subject matter of any of examples 17 to 25 can optionally comprise the fact that, in the method, at least one distributed digital field effect transistor array having a nonuniform distribution of a compensation heating power in the array, optionally a distributed digital metal oxide semiconductor field effect transistor array having a nonuniform distribution of a compensation heating power in the array, is used as the heating structure.

In the case of example 28, the subject matter of any of examples 17 to 27 can optionally comprise the fact that driving the heating structure furthermore comprises actuating a switching device in a compensation circuit, in such a way that the compensation circuit is closed or opened by means of the switching device, wherein the switching device, the heating structure and a supply voltage are connected in series in the compensation circuit.

In the case of example 29, the subject matter of example 28 can optionally comprise the fact that driving the heating structure furthermore comprises negating the information by means of an inverter in the compensation circuit, actuating the switching device by means of an output signal of the inverter.

In the case of example 30, the subject matter of example 28 can optionally comprise the fact that driving the heating structure furthermore comprises converting the information as a digital input signal into an analog output signal by means of a digital-to-analog converter, comparing the analog output signal with a reference voltage by means of a differential amplifier, actuating the switching device in the compensation circuit by means of an output signal of the differential amplifier, wherein the switching device is a transistor.

In the case of example 31, the subject matter of any of examples 20 to 30 can optionally comprise the fact that the power loss of the heating structure is adapted to a power loss of a device provided in the environment of the at least one sensor, such that a temperature influencing of the at least one sensor is kept at a predefined value.

In the case of example 32, the subject matter of example 31 can optionally comprise the fact that adapting the power loss of the heating structure comprises adapting the supply voltage or a resistance value of the resistor to the power loss of the device provided in the environment of the at least one sensor.

In the case of example 33, the subject matter of either of examples 31 and 32 can optionally comprise the fact that the power loss of the heating structure is repeatedly adapted to the power loss of the device provided in the environment of the at least one sensor.

In the case of example 34, the subject matter of any of examples 31 to 33 can optionally comprise the fact that a power loss of a plurality of heating structures is set by means of a batch calibration.

In various exemplary embodiments, a sensor circuit can comprise: at least one sensor for determining a measurement variable, a heating structure, at least one compensation circuit, wherein the compensation circuit is configured to acquire information about a temperature change in an environment of the sensor, and to counteract a temperature change in the sensor on the basis of the information by means of driving the heating structure.

In various exemplary embodiments, what can be achieved is that a temperature change in an environment of a sensor or a temperature change of a sensor can be counteracted by an opposite temperature behavior in the sensor. What can be achieved thereby is that a temperature of at least one sensor can be kept in a predefined temperature range. Furthermore, a fluctuation of an output signal on account of an external temperature influence can be kept in a predefined tolerance range.

In various exemplary embodiments, by way of example, at least one sensor can be provided in order to determine a measurement variable and to provide an output measurement signal. The at least one sensor can be provided in the vicinity of a heating structure. By way of example, a heating structure can be provided below, above, alongside, or at a side of the sensor. By way of example, the heating structure can be connected to the sensor directly, for example in a manner touching it, or indirectly, for example by means of an adhesive layer. Furthermore, a compensation circuit can be provided by means of which information about a temperature change in an environment of the sensor can be acquired.

The information can be present for example as an analog signal or as a digital signal, for example as a sequence of "0" and "1" signals. By way of example, information can be provided as digital information "1" if an external activity or operation of a device is present. By way of example, information can be provided as digital information "0" if no external activity or no operation of a device is present. A heating structure can be driven on the basis of or depending on the information, said heating structure counteracting a temperature change in the sensor. By way of example, if a temperature change is present in an environment of the sensor, for example a temperature increase or a temperature decrease, then a temperature in an environment of the sensor can be altered by means of the heating structure. The temperature in the sensor, or in the package in which the sensor or a plurality of sensors can be provided, can be altered in such a way that the temperature in the sensor or in the sensors is altered oppositely to the external temperature change. In the case of a temperature increase in the sensor or in an environment of a sensor, the temperature in the sensor can be reduced by means of the heating structure. In the case of a temperature decrease in the sensor or in the environment of a sensor, the temperature in the sensor can be increased by means of the heating structure.

In various exemplary embodiments, what can be achieved is that a temperature in the sensor is influenced only to a limited extent by a temperature change in an environment of the sensor.

In various exemplary embodiments, the sensor circuit can furthermore comprise a package, wherein the at least one sensor, the heating structure and the compensation circuit are accommodated in the package.

In various exemplary embodiments, what can be achieved is that, by means of a package design, a plurality of functions can be realized with low costs, small dimensions and a high standardization.

In various exemplary embodiments, the sensor circuit can comprise a plurality of sensors in the package.

In various exemplary embodiments, the sensor can be at least one of a microphone, a temperature sensor, a pressure sensor or a gas sensor.

In various exemplary embodiments, the sensor can also be configured or realized as an acceleration sensor, a force sensor or a torsional moment sensor.

In various exemplary embodiments, a sensor circuit can be provided which comprises a plurality of sensors in a common housing, which is also referred to as a package, which can be realized as a so-called combo-system. By way of example, a combo-system can comprise a microphone and a temperature sensor, a gas sensor and a pressure sensor, a microphone and a pressure sensor, etc. in a common package. In various exemplary embodiments, a package can be provided which can comprise a plurality of sensors, for example three, four or even more sensors. However, it is also possible for only one sensor to be accommodated in a package.

In various exemplary embodiments, the microphone can be used to record ambient sound, speech, music or the like and to provide a microphone signal. Recording or providing a microphone signal can be understood as providing an electrical signal which is dependent on the ambient sound or, in other words, on the sound pressure acting on the microphone. Various types of microphone can be used, for example an electret microphone or some other capacitor microphone. One specific example is a silicon capacitor microphone implemented as a MEMS. That is to say that the membrane and other components that form the microphone can be produced using processing steps and techniques that are usually used in microprocessor production.

Some of the properties of the microphone that establish a relationship between the resulting microphone signal and the acting sound pressure can be tuned by hardware properties of the microphone itself, for example the back volume or the stiffness of a membrane of the microphone.

The sensor can comprise for example a membrane, for example a silicone membrane. In this case, a deflection of the membrane from a rest position can generate an analog signal. The membrane is or comprises a MEMS, for example. Alternatively or in other words, the sensor can be or comprise a MEMS.

In various exemplary embodiments, the at least one sensor can for example furthermore be or comprise a force sensor, an acceleration sensor or a torque sensor or a combination of the types of sensor mentioned.

In various exemplary embodiments, at least one temperature sensor or temperature probe can acquire a temperature value in an environment of a sensor. The temperature sensor can be provided in a package; however, the temperature sensor can be provided in an environment outside the package. The temperature sensor can be provided alongside a further electronic device, for example a sensor. Depending on the temperature value acquired by means of the temperature sensor, a power loss at a heating structure can be set in such a way that, by means of the heating structure, a temperature change around the sensor or at the sensor or at the package can be kept in a predefined tolerance range.

In various exemplary embodiments, the compensation circuit can be configured to counteract the temperature change by means of a change in a power loss of the heating structure.

For illustration, a heating structure in the vicinity of a sensor can generate a power loss of assumedly two watts, for example. A device in an environment of the sensor, for example in a switched-off state, can generate a power loss of assumedly zero watts. If the device in the environment of the sensor is switched on or put into operation and a power loss of two watts, for example, in the form of heat is generated by the device, the sensor can heat up. The power loss of the heating structure can be reduced for example from assumedly two watts to assumedly zero watts and an approximately constant temperature of the sensor can thus be achieved.

In various exemplary embodiments, the compensation circuit can be provided alongside the at least one sensor in the sensor circuit.

What can be achieved is that, as a result of an arrangement of the heating structure alongside the at least one sensor, the temperature in the sensor can be rapidly or efficiently adapted to changing temperature conditions in a sensor environment.

The compensation circuit can be configured to acquire the information about the temperature change in the environment of the sensor in the form of a periodic and/or a discrete switch-on and switch-off sequence, wherein the compensation circuit is furthermore configured to activate or to deactivate the heating structure oppositely to the switch-on and switch-off sequence.

In various exemplary embodiments, what can be achieved is that an external temperature fluctuation can be counteracted by means of an internal temperature fluctuation in the opposite direction.

The compensation circuit can be provided to compensate for a temperature increase in the environment of the sensor by means of reducing the power loss of the heating structure, and to compensate for a temperature reduction in the environment of the sensor by means of increasing the power loss of the heating structure.

In various exemplary embodiments, what can be achieved is that an extremely high temperature that can lead to damage to the sensor can be avoided in the sensor.

The heating structure can comprise at least one variable resistor, wherein the at least one variable resistor generates the power loss, or wherein the heating structure comprises at least one field effect transistor, optionally a metal oxide semiconductor field effect transistor, wherein the at least one field effect transistor is configured to generate the power loss.

What can thus be achieved is that a cost-effective component, for example a resistor, can be used to compensate for a temperature change.

In various exemplary embodiments, a sensor circuit can be provided in which the heating structure, for example an ohmic resistor, can have a resistance value in accordance with the equation $$R = \frac{U}{I}.$$

The variable U can be a supply voltage or reference voltage and the variable I can be a current flowing through the heating structure. In various exemplary embodiments, a sensor circuit can be provided in which a constant supply voltage U can lead to a power loss P as a result of a current I in accordance with the equation P=U*I. The supply voltage U can be an external voltage provided by means of a power supply unit or a battery, for example. The current can comprise a current sequence in the form of a rectangular signal.

In various exemplary embodiments, a sensor circuit can be provided in which a simple circuit construction is able to be realized by means of a supply voltage and a resistor as heating structure.

In various exemplary embodiments, what can be achieved is that the power loss of the heating structure, for example of a resistor or of a variable resistor, can be regulated proportionally to the applied supply voltage. Furthermore, the heating structure can be calibrated to a defined temperature by changing the supply voltage.

In various exemplary embodiments, the heating structure, for example a resistor, can be permanently energized during operation of the at least one sensor. During operation, the resistor can continuously generate a power loss in the form of heat, by means of which for example the at least one sensor can be heated and kept at a predefined temperature.

In various exemplary embodiments, by way of example, a micanite heating element or a ceramic heating element can be used as a heating structure.

The heating structure can comprise at least one distributed digital field effect transistor array, optionally a metal oxide semiconductor field effect transistor array, having a nonuniform distribution of a compensating heating power in the array, wherein the at least one distributed digital field effect transistor array is configured to generate the power loss.

What can be achieved is that an individually adjustable heating power distribution of the heating structure can be realized by means of a distributed digital field effect transistor array. In this regard, by way of example, defined regions of the field effect transistor array can be heated to a greater extent than other regions, which can be utilized for different heating of regions of the sensor. Consequently, in various exemplary embodiments, it is possible to achieve a heating structure which is adjustable individually to one sensor or to a plurality of sensors and which has an increased adaptability of the heating structure to the respective ambient conditions.

The compensation circuit can comprise a switching device, a voltage supply and the heating structure in a series connection.

In various exemplary embodiments, a sensor circuit can be provided in which the switching device can be realized as an electromechanically actuable switch, for example as a relay, as a field effect transistor (FET) or as a bipolar transistor. The switch can be or comprise for example a break contact or a make contact.

The compensation circuit can furthermore comprise an inverter, wherein the inverter is connected upstream of the switching device, and the switching device is an electromechanically actuatable switch. An output of the inverter can be connected to the switching device. The inverter can receive a rectangular signal for example at an input. The signal can be a digital signal and have a zero level or a one level, for example.

The compensation circuit can furthermore comprise a differential amplifier and a digital-to-analog converter, wherein the differential amplifier is connected upstream of the switching device and an input of the differential amplifier is coupled to an output of the digital-to-analog converter, wherein the digital-to-analog converter is configured to acquire the information about the temperature change in the environment of the sensor circuit as a digital signal, wherein the differential amplifier is configured in such a way that an output signal of the differential amplifier activates or deactivates the switching device, and wherein the switching device is a transistor.

External information can be present as a digital signal which can be fed to the digital-to-analog converter. The digital-to-analog converter converts the digital signal into an analog signal, for example into an analog voltage. The analog signal can be fed to one input of a differential amplifier. By way of example, a voltage tapped off in the compensation circuit can be applied to a further input of the differential amplifier. The voltage tapping point can be situated for example between a transistor connected in series with the heating structure and the heating structure, for example between the source terminal of the transistor and the heating structure. The two signals, for example voltage levels, can be compared by means of the differential amplifier and the differential amplifier can output a voltage, for example an amplified input signal, at the output of the differential amplifier depending on the voltage levels present. The voltage that is output can be provided as a control voltage of a transistor. The transistor can comprise a drain terminal, a source terminal and a gate terminal. The output voltage of the differential amplifier can be provided as a gate-source control voltage. If a gate-source control voltage is present at the transistor, then a current can flow between the drain and source terminals of the transistor and the heating structure can be energized by means of the current, such that a power loss in the form of heat can be generated by means of the heating structure. If no gate-source control voltage is present at the transistor, then no current can be formed between the drain and source terminals, such that the heating structure cannot generate any power loss.

In various exemplary embodiments, a voltage subjected to digital-to-analog conversion can be converted into a current by means of the amplifier.

The transistor can be for example a p-channel junction field effect transistor.

The sensor circuit can be provided in a smartphone or in a tablet.

What can thus be achieved is that external temperature influences on a sensor in a smartphone or in a tablet can be compensated for by means of the heating structure.

The sensor circuit can be a MEMS and can comprise for example an application-specific integrated circuit (ASIC).

In various exemplary embodiments, what can be achieved is that it is possible to provide an optimized measuring system by means of which costs can be saved by virtue of a low consumption of materials and/or by virtue of parallel manufacture. Furthermore, in various exemplary embodiments, what can be achieved is that an efficiency of a measuring system can be increased by virtue of a low energy demand and a miniaturization of a MEMS or ASIC.

In various exemplary embodiments, an envelope signal of a radio-frequency power amplifier can be usable as the information or a time division multiple access (TDMA) signal of a power amplifier can be usable as the information.

The envelope can specify an amplitude profile of a wave packet and serve as information about the activity or operation of a device that generates a power loss, for example. In various exemplary embodiments, the power loss can be determined for example from an amplitude profile of a wave packet.

In various exemplary embodiments, a method for compensating for temperature changes can comprise acquiring information about a temperature change in an environment of at least one sensor, driving a heating structure on the basis of the acquired information in order to counteract a temperature change in the at least one sensor.

In various exemplary embodiments, a method can be provided in which the heating structure is driven in such a way that a temperature of at least one sensor is kept at a predefined temperature level, such that fluctuations of an output signal of the at least one sensor on account of the temperature change are kept in a predefined tolerance range.

In various exemplary embodiments, a method can be provided in which a voltage of a voltage source or a resistance of the heating structure is set in such a way that a temperature influence is set to a predefined tolerance range.

In various exemplary embodiments, a method can be provided in which a power loss can be described by means of the equation:

$$P_{loss}=I_{loss}*V_{reference}-\text{ext.activity}*K*V_{reference}$$

Ploss can be a power loss. $I_{loss}$ can be a current loss that can lead to the power loss $P_{loss}$. $V_{reference}$ can be a reference voltage or a supply voltage. $P_{loss}$ is equal to a product of the current loss $I_{loss}$ and the reference voltage $V_{reference}$. $P_{loss}$ is proportional to a product of an external activity ext.activity of at least one device, a gain factor K of an amplifier and the reference voltage $V_{reference}$. The gain factor K indicates the extent to which the power of the input signal of the amplifier is increased (by the gain factor K). The external activity can be for example a sequence of switched-on and switched-off signals, for example a sequence of analog voltage signals or a sequence of digital logic "0" and "1" signals. The external activity can be or comprise a voltage value, for example.

In various exemplary embodiments, a method can be provided in which a power level of a heating structure can be set at a defined value. Furthermore, the power level can be fixed depending on the real conditions, for example by programming a reference voltage $V_{reference}$ or a resistance $R_{heating}$, until the X-talk will possibly attain a minimum. Furthermore, the programming of $V_{reference}$ or $R_{heating}$ can be carried out in the background of operation of the sensor circuit, wherein changing ambient temperature influences can be taken into consideration.

In various exemplary embodiments, acquiring the information can comprise receiving information regarding operation of a power amplifier and/or regarding operation of an antenna in a smartphone or in a tablet.

In various exemplary embodiments, a power loss in the form of heat can be generated during operation of a power amplifier and/or an antenna. The heat can be emitted to or act on a sensor. In various exemplary embodiments, information about an activity or operation of a power amplifier and/or an antenna can be received by means of the sensor circuit in order to perform a compensation of the temperature influencing of the at least one sensor. In various exemplary embodiments, it is also possible to acquire information about the activity or operation of further devices which can provide information about a total power loss of the plurality of further devices.

In various exemplary embodiments, what can be achieved is that interference influences that act on a sensor for example through an antenna or a power amplifier can be reduced to a predefined range or possibly minimized. An error susceptibility of the measuring system vis-à-vis external temperature influences can be reduced as a result.

In various exemplary embodiments, acquiring the information can comprise receiving a radio-frequency power amplifier envelope signal or receiving a time division multiple access (TDMA) signal of a power amplifier.

In various exemplary embodiments, operation or an activity of a power amplifier can be detected by receiving a radio-frequency power amplifier envelope signal, wherein, in the event of receiving a radio-frequency power amplifier envelope signal, by way of example, the heating power can be reduced or the heating structure can be deactivated, and, in the event of not receiving a radio-frequency power amplifier envelope signal, the heating power can be increased or the heating structure can be activated.

In various exemplary embodiments, in the event of a radio-frequency signal being generated, a corresponding envelope signal can be generated, for example with a delay or approximately at the same time. The envelope signal can be used to acquire information about an activity or operation of a power amplifier or a power loss associated therewith.

In various exemplary embodiments, by receiving a time division multiple access (TDMA) signal of a power amplifier, it is possible to determine that point in time at which a switch-on of a power amplifier is performed. In a time division multiple access (TDMA) method, data or signals of different transmitters are transmitted on a channel in defined time segments or time slots. Whenever signals of the power amplifier are transmitted on a channel, a time division multiple access (TDMA) signal can be generated. By receiving the time division multiple access (TDMA) signal of a power amplifier, it is possible to detect an activity or operation of the power amplifier.

In various exemplary embodiments, driving the heating structure can comprise counteracting a temperature increase in the environment of the at least one sensor by means of reducing the power loss of the heating structure, and driving the heating structure can comprise counteracting a temperature decrease in the environment of the at least one sensor by means of increasing the power loss of the heating structure.

In various exemplary embodiments, counteracting a temperature increase in the environment of the at least one sensor can comprise deactivating the heating structure, and counteracting a temperature decrease in the environment of the at least one sensor can comprise activating the heating structure.

In various exemplary embodiments, by means of switching on or switching off the heating structure, it is possible to realize a simple construction and a simple driving of the heating structure.

Acquiring the information and driving the heating structure can be carried out dynamically. Acquiring the information and driving the heating structure can be provided at predefined time intervals.

In various exemplary embodiments, what can be achieved is that, by means of dynamic driving, it is possible to react rapidly to a varying temperature change in an environment of a sensor or it is possible to adapt the power loss of the heating structure more rapidly to a real temperature change in an environment of the sensor.

The heating structure can be driven in such a way that a temperature of at least one sensor is kept in a predefined temperature range, such that fluctuations of an output signal of the at least one sensor on account of the temperature change can be kept in a predefined tolerance range.

In various exemplary embodiments, a method can be provided by means of which a reduction of a thermoacoustic effect can be realized by a reduction of a temperature change in a sensor system, which can consist for example of a microphone and at least one other sensor. In various exemplary embodiments, what can be achieved is that an influencing of the microphone by at least one further sensor can be reduced to a predefined measure. In various exemplary embodiments, a method can be provided in which, by way of example, an audible influencing of the measurement signal of a microphone by at least one further sensor can be reduced to a predefined range, possibly minimized.

A degree of compensation of temperature changes in a range of approximately 80% to approximately 90%, for example of approximately 85%, can be achieved by means of the method.

A damping of an interference variable in a range of approximately 14 dB to approximately 20 dB, for example of approximately 17 dB, can be achieved by means of the method.

In the method, at least one variable resistor or at least one field effect transistor, optionally a metal oxide semiconductor field effect transistor, can be used as the heating structure.

By way of example, a potentiometer can be used as a variable resistor, the resistance value of which can be adjustable.

Furthermore, by way of example, the power loss of the field effect transistor that is converted into heat can be used.

In various exemplary embodiments, in the method, at least one distributed digital field effect transistor array having a nonuniform distribution of a compensation heating power in the array, optionally a distributed digital metal oxide semiconductor field effect transistor array having a nonuniform distribution of a compensating heating power in the array, can be used as the heating structure.

By means of the distributed digital field effect transistor array, it is possible to realize a compensation of external temperature influences which is individually adapted to the sensor. In this regard, by way of example, one region of a sensor, which is provided nearer to a device generating a power loss than another region of the sensor, which is provided further away from the device generating a power loss, can be impinged on to a varying extent by a power loss of the field effect transistor array in the form of heat.

Driving the heating structure can furthermore comprise actuating a switching device in a compensation circuit, in such a way that the compensation circuit is closed or opened by means of the switching device, wherein the switching device, the heating structure and a supply voltage are connected in series in the compensation circuit.

The switching device can be embodied as a make contact or a break contact.

Driving the heating structure can furthermore comprise: negating the information by means of an inverter in the compensation circuit, actuating the switching device by means of an output signal of the inverter.

In various exemplary embodiments, driving the heating structure can furthermore comprise: converting the information as a digital input signal into an analog output signal by means of a digital-to-analog converter, comparing the analog output signal with a reference voltage by means of a differential amplifier, actuating the switching device in the compensation circuit by means of an output signal of the differential amplifier, wherein the switching device is a transistor.

In various exemplary embodiments, the power loss of the heating structure can be adapted to a power loss of a device provided in the environment of the at least one sensor, such that a temperature influencing of the at least one sensor is kept at a predefined value.

Adapting the power loss of the heating structure can comprise adapting a supply voltage value or a resistance value to the power loss of the device provided in the environment of the at least one sensor.

An adaptation of the resistance value can thus be achieved in a simple manner.

In various exemplary embodiments, the power loss of the heating structure can repeatedly, i.e. at defined time intervals, be adapted to the power loss of the device provided in the environment of the at least one sensor.

In various exemplary embodiments, by way of example, by means of a repeated adaptation, for example at defined regular time intervals, it is possible to set an adaptation of the power loss of the heating structure to the power loss of a device provided in the environment of the at least one sensor.

In various exemplary embodiments, a power loss of a plurality of heating structures can be set by means of a batch calibration, for example set partly simultaneously.

In various exemplary embodiments, by way of example, a plurality of compensation circuits can be set in such a way that the heating structure thereof, for example a resistor, can be set by means of an adaptation of the supply voltage value or of an adaptation of the resistance value simultaneously by means of a batch method. In this regard, in various exemplary embodiments, what can be achieved is that a plurality of compensation circuits can be set simultaneously or partly simultaneously.

In various exemplary embodiments, a method can be provided in which a power loss level of an externally provided electronic device and a power loss level of at least one heating structure are coordinated with one another by means of a batch calibration.

Further configurations of the method are evident from the description of the device, and vice versa.

The advantages mentioned herein relate both to exemplary embodiments of the sensor circuit and to exemplary embodiments of the method.

Although illustrative embodiments have been shown and described primarily with reference to specific exemplary embodiments, it should be understood by those familiar with the technical field that numerous modifications can be made thereto regarding configuration and details, without departing from the essence and scope of the invention as defined by the following claims. The scope of the invention is therefore determined by the appended claims, and the intention is to encompass all modifications which come under the literal meaning or fall within the range of equivalence of the claims.

What is claimed is:

1. A sensor circuit, comprising:
   at least one sensor for determining a measurement variable;
   a heating structure; and
   at least one compensation circuit, wherein the compensation circuit is configured to acquire information about a temperature change in an environment of the sensor, and to counteract a temperature change in the sensor on the basis of the information by driving the heating structure,
   wherein a power loss of the heating structure is adapted to a power loss of a device provided in the environment of the at least one sensor, such that a temperature influencing the at least one sensor is kept at a predefined value.

2. The sensor circuit as claimed in claim 1, wherein the sensor is at least one of a microphone, a temperature sensor, a pressure sensor or a gas sensor.

3. The sensor circuit as claimed in claim 1, wherein the compensation circuit is configured to counteract the temperature change by changing a power loss of the heating structure.

4. The sensor circuit as claimed in claim 3, wherein the compensation circuit is configured to compensate for a temperature increase in the environment of the sensor by of reducing the power loss of the heating structure, and configured to compensate for a temperature reduction in the environment of the sensor by increasing the power loss of the heating structure.

5. The sensor circuit as claimed in claim 3, wherein the heating structure comprises at least one variable resistor, wherein the at least one variable resistor generates the power loss, or
   wherein the heating structure comprises at least one field effect transistor configured to generate the power loss.

6. The sensor circuit as claimed in claim 3, wherein the heating structure comprises at least one distributed digital field effect transistor array having a nonuniform distribution of a compensating heating power in the array, wherein the at least one distributed digital field effect transistor array is configured to generate the power loss.

7. The sensor circuit as claimed in claim 1, wherein the compensation circuit is disposed alongside the at least one sensor in the sensor circuit.

8. The sensor circuit as claimed in claim 1, wherein the compensation circuit is configured to acquire the information about the temperature change in the environment of the sensor in the form of a periodic and/or a discrete switch-on and switch-off sequence, and
   wherein the compensation circuit is further configured to activate or to deactivate the heating structure oppositely to the switch-on and switch-off sequence.

9. The sensor circuit as claimed in claim 1,
   wherein the compensation circuit comprises a switching device, a voltage supply and the heating structure in a series connection; and
   wherein the compensation circuit further comprises an inverter, wherein the inverter is connected upstream of the switching device, and the switching device is an electromechanically actuatable switch.

10. The sensor circuit as claimed in claim 9, wherein the compensation circuit further comprises a differential amplifier and a digital-to-analog converter, wherein the differential amplifier is connected upstream of the switching device and an input of the differential amplifier is coupled to an output of the digital-to-analog converter, wherein the digital-to-analog converter is configured to acquire the information about the temperature change in the environment of the sensor circuit as a digital signal,
   wherein the differential amplifier is configured to produce an output signal that activates or deactivates the switching device, and
   wherein the switching device is a transistor.

11. The sensor circuit as claimed in claim 1, wherein the sensor circuit is provided in a smartphone or in a tablet.

12. The sensor circuit as claimed in claim 1, wherein the sensor circuit is a Micro-Electro-Mechanical System (MEMS) or an application-specific integrated circuit (ASIC).

13. The sensor circuit as claimed in claim 1, wherein the information comprises an envelope signal of a radio-frequency power amplifier or a time division multiple access (TDMA) signal of a power amplifier.

14. A method for compensating for temperature changes, comprising:

acquiring information about a temperature change in an environment of at least one sensor; and driving a heating structure on the basis of the acquired information in order to counteract a temperature change in the at least one sensor, wherein a power loss of the heating structure is adapted to a power loss of a device provided in the environment of the at least one sensor, such that a temperature influencing the at least one sensor is kept at a predefined value.

15. The method as claimed in claim 14, wherein acquiring the information comprises receiving information regarding operation of a power amplifier and/or regarding operation of an antenna in a smartphone or in a tablet.

16. The method as claimed in claim 14, wherein driving the heating structure comprises counteracting a temperature increase in the environment of the at least one sensor by reducing a power loss of the heating structure, and wherein driving the heating structure comprises counteracting a temperature decrease in the environment of the at least one sensor by increasing the power loss of the heating structure;

wherein counteracting a temperature increase in the environment of the at least one sensor comprises deactivating the heating structure; and wherein counteracting a temperature decrease in the environment of the at least one sensor comprises activating the heating structure.

17. The method as claimed in claim 14, wherein acquiring the information and driving the heating structure are carried out dynamically.

18. The method as claimed in claim 14, wherein adapting the power loss of the heating structure comprises adapting a supply voltage or a resistance value of a resistor to the power loss of the device provided in the environment of the at least one sensor.

19. The method as claimed in claim 18, wherein the power loss of the heating structure is repeatedly adapted to the power loss of the device provided in the environment of the at least one sensor.

* * * * *